(12) United States Patent
Ichim

(10) Patent No.: US 10,383,895 B2
(45) Date of Patent: Aug. 20, 2019

(54) STIMULATION OF THERAPEUTIC ANGIOGENESIS BY T REGULATORY CELLS

(71) Applicant: Viera Bioscience, Inc., Rancho Santa Fe, CA (US)

(72) Inventor: Thomas Ichim, San Diego, CA (US)

(73) Assignee: VIERA BIOSCIENCE, INC., Rancho Santa Fe, CA (US)

(*) Notice: Subject to any disclaimer, the term of this patent is extended or adjusted under 35 U.S.C. 154(b) by 49 days.

(21) Appl. No.: 15/436,400

(22) Filed: Feb. 17, 2017

(65) Prior Publication Data

US 2017/0239293 A1 Aug. 24, 2017

Related U.S. Application Data

(60) Provisional application No. 62/297,071, filed on Feb. 18, 2016.

(51) Int. Cl.
| | |
|---|---|
| *A61K 35/17* | (2015.01) |
| *C12N 5/0783* | (2010.01) |
| *C07K 14/71* | (2006.01) |

(52) U.S. Cl.
CPC ............ *A61K 35/17* (2013.01); *C12N 5/0637* (2013.01); *C12N 2501/2302* (2013.01); *C12N 2501/51* (2013.01); *C12N 2501/515* (2013.01); *C12N 2502/1352* (2013.01)

(58) Field of Classification Search
None
See application file for complete search history.

(56) References Cited

PUBLICATIONS

Zouggari et al (Circulation, 2009, 120: 1415-1425).*
D'Alessio et al (Am. J. Respir. Cell. Mol. Biol., 52(5): 603-610, originally published on Oct. 2, 2014).*
Sharir et al (Card. Res. 2014, 103: 585-596).*
Hellingman et al (2012, J. Cell. Mol. Med., 16(2): 328-336) (Year: 2012).*
Singer et al (Front. Immunol. 2014, vol. 5, article 46, pp. 1-10) (Year: 2014).*
Gupta et al (J. Transl. Med. 2013, 11: 143, pp. 1-11) (Year: 2013).*
Kleinschnitz et al (Blood, 2013, 121(4): 679-691) (Year: 2013).*
Nadig et al (Nature Medicine, 2010, 16(7): 809-813) (Year: 2010).*
Xu et al (Sci. World Journal, 2013, article ID 174373, pp. 1-8) (Year: 2013).*
Rota et al (Neurol. Sci., 2006, 27: 33-39) (Year: 2006).*
Riley et al (Immunity, 2009, 30: 656-665) (Year: 2009).*
Bruno, A. et al. Orchestration of Angiogenesis by Immune Cells, Frontiers in Oncology, 2014, 4, 6.
D'Alessio, F. et al., Lung Angiogenesis Requires CD4+ Forkhead Homeobox Protein-3 + Regulatory T Cells, Am J Resp Cell Mol Biol, 2015, 52, 603-610, orig publ online Oct. 2, 2014.
Hellingman, A. et al., A limited role for regulatory T cells in post-ischemic neovascularization, J Cell and Mol Med, 2012, 16, 328-336.
Li, P. et al., Adoptive regulatory T-cell therapy protects against cerebral ischemia, Annals of Neurology, 2013, 74, 458-471.
Planas, A. et al., Regulatory T cells protect the brain after stroke, Nature Med, 2009, 15, 138-139.
Silvestre, J. et al., Post-ischaemic neovascularization and inflammation, Cardiovascular Res, 2008, 78, 242-249.
Tolar, J. et al., Immune regulatory cells in umbilical cord blood: T regulatory cells and mesenchymal stromal cells, British J Haemotol, 2009, 147, 200-206.
Zhong, Q. et al., Effector T Cells and Ischemia-Induced Systemic Angiogenesis in the Lung, Am J Resp Cell Mol Biol, 2016, 54, 394-401.
Zouggari, Y. et al., Regulatory T Cells Modulate Postischemic Neovascularization, Circulation, 2009, 120, 1415-1425.
Zouggari, Y. et al., D022 Natural CD4/CD25/Foxp3 regulatory t cells modulate post-ischemic inflammatory response: role in neovascularization, Archives of Cardiovascular Disease, 2009, 102, S44.
PCT Invitation to Pay Additional Search Fees in related application PCT/US2017/018417, dated May 30, 2017.
Aschenbrenner, K., et al., Nat Immunol, 2007. 8(4): p. 351-8.
Bai, L., et al., Nat Neurosci, 2012. 15(6): p. 862-70.
Barbay, V., et al., Angiogenesis, 2015. 18(2): p. 191-200.
Bluestone, J.A., et al., J Clin Invest, 2015. 125(6): p. 2250-60.
Brea, D., et al., J Cell Mol Med, 2014. 18(8): p. 1571-9.
Brunstein, C.G., et al., Blood, 2011. 117(3): p. 1061-70.
Cahill, E.F., et al., Stem Cell Res Ther, 2015. 6: p. 19.
Coutu, D.L., M. Francois, and J. Galipeau, Blood, 2011. 117(25): p. 6801-12.
Dungan, L.S., et al., Eur J Immunol, 2014. 44(10): p. 2903-17.
Engela, A.U., et al., Clin Exp Immunol, 2013. 173(2): p. 343-54.
Erkers, T., et al., Stem Cells Dev, 2013. 22(19): p. 2596-605.
Facciabene, A., et al., Nature, 2011. 475(7355): p. 226-30.
Facciabene, A., G.T. Motz, and G. Coukos, Cancer Res, 2012. 72(9): p. 2162-71.
Fallarino, F., et al., Nat Immunol, 2003. 4(12): p. 1206-12.
Fong, C.Y., et al., J Cell Biochem, 2012. 113(2): p. 658-68.
Gianni-Barrera, R., et al., Biochem Soc Trans, 2014. 42(6): p. 1637-42.
Giatromanolaki, A., et al., Gynecol Oncol, 2008. 110(2): p. 216-21.
He, S., et al., Arterioscler Thromb Vasc Biol, 2010. 30(12): p. 2621-30.
Hoffmann, J., et al., Thorac Cardiovasc Surg, 2010. 58(3): p. 136-42.
Iwase, T., et al., Cardiovasc Res, 2005. 66(3): p. 543-51.
Kingsley et al., 2002 J. Immunol. 168: 1080.
Kinnaird, T., et al., Circ Res, 2004. 94(5): p. 678-85.
Kinnaird, T., et al., Circulation, 2004. 109(12): p. 1543-9.
Kwon, H.M., et al., Vascul Pharmacol, 2014. 63(1): p. 19-28.
Kwon, M.S., et al., J Neurochem, 2014. 131(2): p. 206-18.

(Continued)

*Primary Examiner* — Daniel E Kolker
(74) *Attorney, Agent, or Firm* — Knobbe, Martens, Olson & Bear LLP

(57) ABSTRACT

Disclosed herein are new, useful, and non-obvious means of stimulating therapeutic angiogenesis, or conditions favorable for stimulation of therapeutic angiogenesis utilizing T regulatory cells. One disclosed method includes administering a population of T regulatory cells into an area of hypoxia to stimulate angiogenesis. T regulatory cells are generated and expanded by culture with mesenchymal stem cells, with either population or both populations together administered into the hypoxic area.

8 Claims, 7 Drawing Sheets

(56) References Cited

PUBLICATIONS

Lai, W.T., V. Krishnappa, and D.G. Phinney, Stem Cells, 2011. 29(7): p. 1102-11.
Lee, E.S., et al., PLoS One, 2015. 10(9): p. e0138846.
Luz-Crawford, P., et al., Stem Cell Res Ther, 2013. 4(3): p. 65.
Matsumoto, K., et al., Int Heart J, 2011. 52(6): p. 382-7.
Meng et al., 2007, J. Trans. Med. 5:57.
Mills, C.D., et al., J Immunol, 2000. 164(12): p. 6166-73.
Montes, R., et al., Cell Res, 2009. 19(6): p. 698-709.
Na, S.Y., et al., Stroke, 2015. 46(1): p. 212-20.
Nakamura et al., 2001 J. Exp. Med. 194: 629-644.
Nummer, D., et al., J Natl Cancer Inst, 2007. 99(15): p. 1188-99.
Onodera, T., et al., J Immunol, 2009. 183(9): p. 5608-14.
Pucino, V., et al., Chem Immunol Allergy, 2014. 99: p. 155-69.
Sakaguchi, 2004 Ann. Rev. Immunol. 22: 531.
Saxena, A., et al., Am J Physiol Heart Circ Physiol, 2014. 307(8): p. H1233-42.
Shen, C., et al., Mol Med Rep, 2015. 12(1): p. 20-30.
Silva Dos Santos, D., et al., Cell Med, 2014. 7(1): p. 25-35.
Spence, S., et al., Immunity, 2013. 38(1): p. 66-78.
Stubbe, T., et al., J Cereb Blood Flow Metab, 2013. 33(1): p. 37-47.
Sun, T., et al., Oncol Res, 2014. 21(5): p. 227-35.
Tang, T.T., et al., Basic Res Cardiol, 2012. 107(1): p. 232.
Treacy, O., et al., Am J Transplant, 2014. 14(9): p. 2023-36.
Trenado et al., 2002 J. Clin. Invest. 112(11): 1688-1696.
Walenda, T., et al., Exp Hematol, 2011. 39(6): p. 617-28.
Wang, Z.X., et al., Mol Cell Biochem, 2015. 400(1-2): p. 163-72.
Weirather, J., et al., Circ Res, 2014. 115(1): p. 55-67.
Xing, Y., et al., Genes Cells, 2016.
Yodoi, K., et al., Hypertension, 2015. 65(4): p. 889-95.
Zhan, H.L., et al., Asian Pac J Cancer Prev, 2012. 13(3): p. 867-72.
Zhou, Y., et al., Cardiovasc Res, 2015. 107(1): p. 98-107.
Zou, Q., et al., PLoS One, 2016. 11(2): p. e0149023.

* cited by examiner

STIMULATION OF THERAPEUTIC ANGIOGENESIS BY T REGULATORY CELLS

CROSS-REFERENCE TO RELATED APPLICATIONS

The present application claims the benefit of priority to U.S. Provisional Patent Application No. 62/297,071, filed Feb. 18, 2016, the disclosure of which is incorporated by reference herein in its entirety.

FIELD

The invention pertains to the field of immunology, more specifically, the invention pertains to the use of T regulatory cells, classically known as immunological cells, to stimulate angiogenesis. The invention pertains to utilization of cells to stimulate angiogenesis, more particularly, the invention relates to utilization of immune cells to stimulate angiogenesis, more particularly, the invention relates to utilization of T regulatory cells to stimulating therapeutic angiogenesis, as well as synergies between T regulatory cells and stem cells at stimulating angiogenesis.

BACKGROUND

T regulatory (Treg) cells are an essential component of the immune system protecting the body against autoimmune attack. This is illustrated by early studies in which neonatally thymectomized mice suffered from systemic autoimmunity, which were rescued by transfer of CD4 cells. Subsequent studies identified the Treg phenotype as possessing the IL-2 receptor CD25, which is somewhat problematic given that this receptor is found on activated T cells as well. Peripheral blood contains a small population of T cell lymphocytes that express the T regulatory phenotype, for example, positive for both CD4 and CD25 antigens. There are several subsets of Treg cells. One subset of regulatory cells develops in the thymus. Thymic derived Treg cells function by a cytokine-independent mechanism, which involves cell to cell contact. They are essential for the induction and maintenance of self-tolerance and for the prevention of autoimmunity (Shevach, 2000 Annu. Rev. Immunol. 18: 423-449). These regulatory cells prevent the activation and proliferation of autoreactive T cells that have escaped thymic deletion or recognize extrathymic antigens, thus they are critical for homeostasis and immune regulation, as well as for protecting the host against the development of autoimmunity. Thus, immune regulatory $CD4^+$ $CD25^+$ T cells are often referred to as "professional suppressor cells."

Naturally arising $CD4^+CD25^+$ Treg cells are a distinct cell population of cells that are positively selected on high affinity ligands in the thymus and that have been shown to play an important role in the establishment and maintenance of immunological tolerance to self-antigens. Deficiencies in the development and/or function of these cells have been associated with severe autoimmunity in humans and various animal models of congenital or induced autoimmunity.

Treg cells manifest their tolerogenic effects directly via cell-to-cell contact or indirectly via soluble factors. Although the suppressive mechanisms of these cells remain to be fully elucidated, blockade of IL-2 expression in effector T cells (Teff), physical elimination of Teff cells, induction of tolerogenic dendritic cells (DCs) via CTLA-4/ B7 axis, and inhibition of Teff cells via TGF-β and IL-10 are some of the mechanisms that have been implicated to date. It also has been shown that reverse signaling through CTLA-4/CD80 into Teff cells plays an important role in their inhibition by Treg cells. Similarly, interactions between CTLA-4 on Treg cells and CD80 on DCs can result in reverse signaling and upregulation of the indoleamine dioxygenase enzyme that is involved in tolerance via the regulation of tryptophan metabolism.

Treg cells can also be generated by the activation of mature, peripheral $CD4^+$ T cells. Studies have indicated that peripherally derived Treg cells mediate their inhibitory activities by producing immunosuppressive cytokines, such as transforming growth factor-beta (TGF-β) and IL-10 (Kingsley et al., 2002 J. Immunol. 168: 1080; Nakamura et al., 2001 J. Exp. Med. 194: 629-644). Treg cells have been described in the literature as being hypoproliferative in vitro (Sakaguchi, 2004 Ann. Rev. Immunol. 22: 531). Trenado et al. provided the first evaluation of the therapeutic efficacy of ex vivo activated and expanded $CD4^+CD25^+$ regulatory cells in an in vivo mouse model of disease (Trenado et al., 2002 J. Clin. Invest. 112(11): 1688-1696). To date, all known activities of Treg cells have been related to immune modulation.

SUMMARY

Treg cells are known to inhibit immune responses, playing a key role in protection against autoimmunity, and promotion of neoplastic immune evasion. The direct stimulation of angiogenesis by Treg cells has not been evaluated. Accordingly, provided herein are methods and systems for the stimulation of angiogenesis by Treg cells. In some embodiments, in vitro human umbilical vein endothelial cell (HUVEC) model is used for the stimulation of angiogenesis. In some embodiments, co-culture of allogeneic umbilical cord blood $CD4^+CD25^+$ Treg cells results in stimulation of HUVEC proliferation. In some embodiments, stimulation of HUVEC proliferation is associated with production of vascular endothelial growth factor (VEGF). In some embodiments, VEGF production is blocked by addition of anti-CTLA4 antibody.

In some embodiments is provided a method of expanding Treg cells using anti-CD3 anti-CD28 beads and IL-2. In some embodiments, expansion of Treg further includes the addition of mesenchymal stem cells (MSC), which results in maintenance of endothelial cell stimulatory properties. In some embodiments, expansion of Treg with MSCs provides a larger expansion as compared to expansion without MSCs.

In some embodiments is provided an in vivo treatment of an immune competent model of critical limb ischemia. In some embodiments, administration of in vitro expanded Treg results in limb salvage in the in vivo model, whereas treatment with control T cells or human fibroblasts does not result in limb salvage. Accordingly, some embodiments provided herein relate to methods of Treg-based angiogenesis as a means of addressing ischemic disease.

Some embodiments disclosed herein relate to a method of stimulating angiogenesis. In some embodiments, the method includes obtaining a population of cells. In some embodiments, the population of cells includes T regulatory cells. In some embodiments, the population of cells containing T regulatory cells includes one or more peripheral blood mononuclear cells, cord blood, menstrual blood, or adipose derived stromal vascular fraction cells.

In some embodiments, the method includes selecting the T regulatory cells from the population of cells. In some embodiments, the method includes activating the T regulatory cells to enhance angiogenic activity of the T regulatory cells. In some embodiments, activating the T regulatory cells includes exposing the T regulatory cells to one or more of vasoactive intestinal peptide, IL-10, TGF-β, mesenchymal stem cell conditioned media, mesenchymal stem cell derived exosomes, brain-derived neurotrophic factor (BDNF), human chorionic gonadotropin, vascular endothelial growth factor (VEGF), CD3 and CD28 antibodies, hypoxic conditions, angiopoietin, or rapamycin. In some embodiments, the T regulatory cells are activated by culture with mesenchymal stem cells. In some embodiments, the mesenchymal stem cells are obtained from one or more of adipose tissue, bone marrow, tooth pulp, hair follicle, endometrium, menstrual blood, peripheral blood, omentum, skin, cord blood, Wharton's jelly, placenta, or fallopian tube. In some embodiments, the mesenchymal stem cells are expanded purified mesenchymal stem cells expressing one or more of CD44, CD90, CD105, CD73, VEGFR2, or TEM-1.

In some embodiments, the method includes administering the T regulatory cells to a patient in need of therapy. In some embodiments, the patient in need of therapy has ischemic tissue. In some embodiments, the ischemic tissue is a limb of a patient suffering from one or more of peripheral artery disease, critical limb ischemia, coronary artery disease, or heart disease. In some embodiments, the patient in need of therapy suffers from neovascular lesions. As described herein, a lesion is a region in an organ or tissue that has suffered damage through injury or disease. A neovascular lesion is a lesion associated with the formation of new blood vessels. Neovascular lesions are common in the choroid of the retina, including subfoveal neovascular lesions. Thus, in some embodiments provided herein is a method of repairing a choroidal neovascular lesion. Other neovascular lesions may also be repaired using the methods provided herein. In some embodiments, the T regulatory cells are administered in an amount of about 2×10$^6$ cells. In some embodiments, the T regulatory cells inhibit proliferation of naïve T cells stimulated with a signal that activates proliferation. In some embodiments, the signal that activates proliferation includes one or more of anti-CD3 beads, anti-CD28 beads, concanavalin A, phytohemagglutinin (PHA), or stimulation with alloreactive antigen presentation cells. In some embodiments, the T regulatory cells express one or more of glucocorticoid-induced TNFR-related (GITR) ligand, neuropilin-1, CTLA-4, CD25, CD105, membrane bound TGF-β, Foxp3, CD39, CD73, CD127, glycoprotein A repetitions predominant (GARP).

Some embodiments disclosed herein relate to a method of stimulating angiogenesis. In some embodiments, the method includes administering a T regulatory cell into an ischemic tissue. In some embodiments, the ischemic tissue is a limb of a patient suffering from one or more of peripheral artery disease, critical limb ischemia, coronary artery disease, or heart disease. In some embodiments, the T regulatory cell expresses the marker CD25 or CTLA4. In some embodiments, the T regulatory cell inhibits proliferation of an activated T cell by more than 25% at a ratio of 1 T regulatory cell to 1 activated T cell. T In some embodiments, the T regulatory cell is derived from cord blood, peripheral blood, menstrual blood, or mobilized peripheral blood. In some embodiments, activation of said T regulatory cell is achieved by one or more of IL-2, rapamycin, anti-CD3 antibody, or anti-CD28 antibody. In some embodiments, the T regulatory cell is cultured with mesenchymal stem cells.

Some embodiments disclosed herein relate to a method of expanding T regulatory cells. In some embodiments, the method includes culturing a population of cells including T regulatory cells. In some embodiments, the method includes enriching CD25+ cells. In some embodiments, the population of cells containing T regulatory cells includes one or more of peripheral blood mononuclear cells, cord blood, menstrual blood, or adipose derived stromal vascular fraction cells. In some embodiments, the method further includes culturing the population of cells with a mesenchymal stem cell feeder layer.

BRIEF DESCRIPTION OF THE DRAWINGS

The description herein is understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
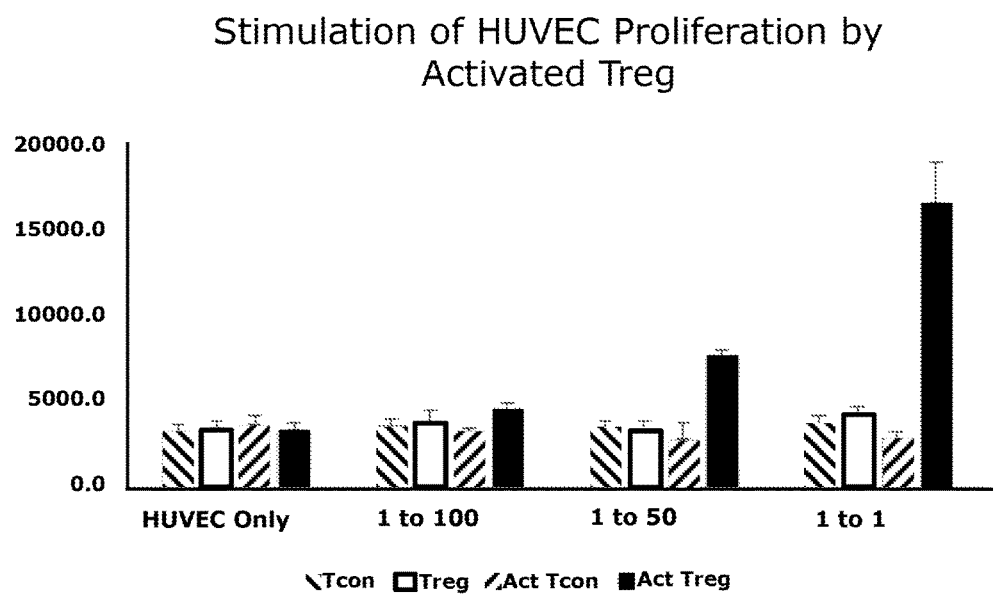
FIG. 1 illustrates the results of stimulation of human umbilical vein endothelial cell (HUVEC) proliferation by activated T regulatory (Treg) cells in an embodiment described herein.

Unless defined otherwise, all technical and scientific terms used herein have the same meaning as is commonly understood by one of ordinary skill in the art. All patents, applications, published applications, and other publications referenced herein are expressly incorporated by reference in their entireties unless stated otherwise. In the event that there is a plurality of definitions for a term herein, those in this section prevail unless stated otherwise.

As used herein, a "normal, healthy individual" or "normal, healthy subject" refers to a subject that does not have the specific disease, disorder or condition being tested.

As used herein, "a subject in need thereof" refers to a subject susceptible to, at risk of, or presenting with a specified disease, disorder, or condition.

As used herein, "susceptible" and "at risk" refer to having little resistance to a certain disease, disorder or condition, including being genetically predisposed, having a family history of, and/or having symptoms of the disease, disorder or condition.

As used herein, "prevent," "preventing," "prevention" and grammatical variations thereof refers to a method of partially or completely delaying or precluding the onset or recurrence of a disorder or condition and/or one or more of its attendant symptoms or barring an animal from acquiring or reacquiring a disorder or condition or reducing an animal's risk of acquiring or re-acquiring a disorder or condition or one or more of its attendant symptoms.

As used herein, the term "reducing" in relation to a particular trait, characteristic, feature, biological process, or phenomena refers to a decrease in the particular trait, characteristic, feature, biological process, or phenomena. The trait, characteristic, feature, biological process, or phenomena can be decreased by 5%, 10%, 15%, 20%, 25%, 30%, 35%, 40%, 45%, 50%, 55%, 60%, 65%, 70%, 75%, 80%, 85%, 90%, 95%, 100% or greater than 100%.

As used herein, the terms "treat," "treating," "treatment" and grammatical variations thereof includes partially or completely delaying, alleviating, mitigating or reducing the intensity of one or more attendant symptoms of a disorder or condition and/or alleviating, mitigating or impeding one or more causes of a disorder or condition. Treatments according to the disclosure may be applied preventively, prophylactically, palliatively or remedially.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some alternatives, the subject is human. As used herein, "a subject in need thereof" refers to a subject susceptible to, at risk of, or presenting with a specified disease, disorder, or condition.

The present invention finds use in veterinary and medical applications as well as in research. Suitable subjects include both avians and mammals. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, and etc. Human subjects include neonates, infants, juveniles, and adults. In other embodiments, the subject is an animal model of ischemia. In certain embodiments, the subject has or is at risk for diabetes (e.g., Type I or Type II diabetes). In other embodiments, the subject has cardiovascular disease or has experienced ischemia or stroke. In still other embodiments, the subject is at risk for ischemia. In further embodiments, the subject is in need of increase angiogenesis and/or arteriogenesis.

As used herein, the term "ischemia" refers to an event that causes a cell, tissue, or organ to receive an inadequate supply of oxygen.

As used herein, the term "angiogenesis" refers to the expansion of current blood vessels or the creation of new blood vessels. "Physiological angiogenesis" is coordinated by complex molecular and cellular mechanisms and is necessary for optimum vascular endothelial health. As used herein "active angiogenesis" refers to the expansion of current blood vessels or the creation of new blood vessels above normal/regular vascular repair; that is vascular repair in a subject not having angiogenesis.

As used herein, "T regulatory cells" or "Treg cells" is a subpopulation of T cells, and refers to a type of T cell that can down regulate immune system. Also, a regulatory T cell can be interchangeably used with Treg cell, $CD4^+CD25^+$ cell, or $CD4^+CD25^+Foxp3^+$ cell. The Treg cell includes both of natural or constitutive regulatory T cell and adaptive or inducible regulatory T cell.

As used herein, "effector T cells" or "Teff cells" refer to T cells (T lymphocytes) that carry out the function of an immune response. In one embodiment, the Teff cells are $CD3^+$ with $CD4^+$ or $CD8^+$. Teff cells may secrete, contain or express effector markers such as IFN-γ, granzyme B and ICOS (but it will be appreciated by persons skilled in the art that Teff cells are not fully restricted to these phenotypes).

Treg cells are a fundamental component of the immune system, possessing ability to recognize and inhibit responses to self-antigens (Bluestone, J. A., et al., J Clin Invest, 2015. 125(6): p. 2250-60). Specifically, when the immune system is formed, Teff cells that recognize self-antigens are deleted in the thymus in a process termed negative selection. Sometimes Teff cells that recognize self-antigens "leak" or escape the process of negative selection, thus possessing ability to induce autoimmune conditions by attacking self-antigens. Examples of autoimmune conditions include Type 1 diabetes, in which Teff cells attack GAD65 antigens in the pancreatic insulin promoting cells, multiple sclerosis, in which Teff cells attack myelin basic protein, or rheumatoid arthritis in which Teff cells attack collagen II protein. In order to protect the body from systemic autoimmunity, Treg cells are generated in the thymus, however, instead of being deleted when they recognize self-antigens in the thymus, they are given a "survival signal" upon recognition of self-antigens (Aschenbrenner, K., et al., Nat Immunol, 2007. 8(4): p. 351-8). In this manner, if Teff cells recognizing self-antigens escape the thymus, a back-up against autoimmunity is Treg cells, which specifically block Teff cells from mediating their effects. The possibility that Treg cells may possess other functions outside of immune modulation was suggested by studies in the area of cancer. In one aspect it was demonstrated that increased number of Treg cells is associated with enhanced tumor angiogenesis (Zhan, H. L., et al., Asian Pac J Cancer Prev, 2012. 13(3): p. 867-72; Giatromanolaki, A., et al., Gynecol Oncol, 2008. 110(2): p. 216-21; Pucino, V., et al., Chem Immunol Allergy, 2014. 99: p. 155-69).

Another sphere of research suggests that depletion of Treg cells in cancer reduces tumor angiogenesis (Facciabene, A., et al., Nature, 2011. 475(7355): p. 226-30). The interaction between Treg cells and tumors is well known and is believed to be dependent on various tumor specific factors, including expression of Treg-attracting addressins that cause selective homing to tumors (Nummer, D., et al., J Natl Cancer Inst, 2007. 99(15): p. 1188-99). Although a suggestion is made that Tregs may stimulate angiogenesis, the possibility that Tregs inhibit Th1 cells, which are potent suppressors of angiogenesis, in part through IP-10 production (Nummer, D., et al., J Natl Cancer Inst, 2007. 99(15): p. 1188-99), can also explain previous associative studies. For example, cytokines produced by Th1 cells such as interferon gamma can inhibit generation of M2 macrophages (Dungan, L. S., et al., Eur J Immunol, 2014. 44(10): p. 2903-17; Spence, S., et al., Immunity, 2013. 38(1): p. 66-78), which are proangiogenic (Barbay, V., et al., Angiogenesis, 2015. 18(2): p. 191-200), and support production of M1 macrophages (Mills, C. D., et al., J Immunol, 2000. 164(12): p. 6166-73), which are anti-angiogenic (Xing, Y., et al., Genes Cells, 2016; Sun, T., et al., Oncol Res, 2014. 21(5): p. 227-35). In some embodiments, Treg cells exhibit improved biodistribution because they are small than mesenchymal stem cells. Because of the improved biodistribution, Treg cells are capable of contributing to inhibition and exhibit improved ability to selectively home to inflammation.

In non-neoplastic conditions, Treg cells have been shown to be associated with therapeutic effects on diverse ischemic conditions such as: a) cardiac infarct (Weirather, J., et al., Circ Res, 2014. 115(1): p. 55-67; Tang, T. T., et al., Basic Res Cardiol, 2012. 107(1): p. 232; Matsumoto, K., et al., Int Heart J, 2011. 52(6): p. 382-7); b) stroke (Stubbe, T., et al., J Cereb Blood Flow Metab, 2013. 33(1): p. 37-47; Brea, D., et al., J Cell Mol Med, 2014. 18(8): p. 1571-9; Na, S. Y., et al., Stroke, 2015. 46(1): p. 212-20); and c) aortic aneurysms (Yodoi, K., et al., Hypertension, 2015. 65(4): p. 889-95; Zhou, Y., et al., Cardiovasc Res, 2015. 107(1): p. 98-107). Interestingly, while the case of cancer Treg cells are associated with enhanced angiogenesis (Facciabene, A., G. T. Motz, and G. Coukos, Cancer Res, 2012. 72(9): p. 2162-71), in non-cancer conditions it appears that Tregs endow therapeutic activities through suppression of inflammation, MMP activity and actually inhibiting angiogenesis (Zhou, Y., et al., Cardiovasc Res, 2015. 107(1): p. 98-107; Saxena, A., et al., Am J Physiol Heart Circ Physiol, 2014. 307(8): p. H1233-42).

Accordingly, some embodiments relate to a method of stimulating angiogenesis. In some embodiments, the method includes obtaining a population of cells including T regulatory cells. Obtaining a population of Treg cells includes obtaining a population of cells including peripheral blood mononuclear cells obtained from cord blood, menstrual blood, or that are adipose-derived stromal vascular fraction cells. In some embodiments, said cells may be obtained from a subject directly, or may be obtained from a culture. Obtaining cells directly from a subject includes obtaining cord blood, menstrual blood, human umbilical vein endothelial cells, or adipose-derived stromal vascular fraction cells directly from the subject. Obtaining cells from a culture includes using an established cell culture of HUVEC cells, mononuclear cells, or other cells obtained from a subject or commercially available. In some embodiments, obtaining a population of cells includes isolating from a cell culture cells that are expressive of one or more of glucocorticoid-induced TNFR-related (GITR) ligand, neuropilin-1, CTLA-4, CD25, CD105, membrane bound TGF-β, Foxp3, CD39, CD73, CD127, glycoprotein A repetitions predominant (GARP). In some embodiments, obtaining a population of Treg cells may include a biopsy.

In some embodiments, the method further includes selecting T regulatory cells from said population of cells to obtain a population of isolated Treg cells. Selecting Treg cells includes isolating those cells that are expressive of a particular marker. In some embodiments, the marker includes one or more of glucocorticoid-induced TNFR-related (GITR) ligand, neuropilin-1, CTLA-4, CD25, CD105, membrane bound TGF-β, Foxp3, CD39, CD73, CD127, glycoprotein A repetitions predominant (GARP). Isolating cells that are expressive of a marker can be accomplished by standard cell detection techniques, including, for example, flow cytometry, cell sorting, immunocytochemistry, fluorescence activated cell sorting, magnetic activated cell sorting, examination of the morphology of the cells using microscopy, or by measuring changes in gene expression using techniques such as PCR or gene expression profiling.

As used herein, "isolating" cells means to remove at least 20%, 30%, 40%, 50%, 60%, 70%, 80%, 90%, 95% or 99% of the cells with which the cells are normally associated. A cell from a subject is "isolated" when it is present in a population of cells that comprises fewer than 50% of the cells with which the cell is normally associated.

As used herein, the term "population of isolated cells" means a population of cells that is substantially separated from other cells of the tissue or of the tissue culture from which the population of cells is derived. A cell is "isolated" if at least 50%, 60%, 70%, 80%, 90%, 95%, or at least 99% of the cells with which the population of cells, or cells from which the population of cells is derived are removed from the cell, during isolation the cell.

In some embodiments, the method further includes activating said T regulatory cells to enhance angiogenic activity of said T regulatory cells. As used herein "activating Treg cells" includes stimulating angiogenic activity of Treg cells, inducing angiogenic activity of Treg cells, or increasing angiogenic activity of Treg cells. As used herein "activated Treg cells" are Treg cells that illicit an angiogenic response. In some embodiments, activating Treg cells includes exposing Treg cells to an activating agent or culture condition that stimulates angiogenic activity of the Treg cells. As used herein, "activating agent" or "activating condition" includes vasoactive intestinal peptide, IL-10, TGF-β, mesenchymal stem cell conditioned media, mesenchymal stem cell derived exosomes, brain-derived neurotrophic factor (BDNF), human chorionic gonadotropin, vascular endothelial growth factor (VEGF), CD3 and CD28 antibodies, hypoxic conditions, angiopoietin, rapamycin, or mesenchymal stem cells. Accordingly, in some embodiments, activating Treg cells includes exposing Treg cells to one or more of vasoactive intestinal peptide, IL-10, TGF-β, mesenchymal stem cell conditioned media, mesenchymal stem cell derived exosomes, brain-derived neurotrophic factor (BDNF), human chorionic gonadotropin, vascular endothelial growth factor (VEGF), CD3 and CD28 antibodies, hypoxic conditions, angiopoietin, or rapamycin. In some embodiments, the Treg cells are exposed to mesenchymal stem cells.

In some embodiments, the method further includes administering said T regulatory cells in a patient in need of therapy or treatment. As used herein, a "patient in need" or a "subject in need" refers to a subject identified as in need of a therapy or treatment, and refers to a subject susceptible to, at risk of, or presenting with a specified disease, disorder, or condition. In some embodiments, a subject in need is a subject susceptible to, at risk of, or presenting with ischemia. In some embodiments, the ischemia is a result of an ischemic event or ischemic injury. As used herein, an "ischemic event" or an "ischemic injury" refers to any instance that results or could result in a deficient supply of blood to a tissue, and could include, for example, hypoglycemia, tachycardia, atherosclerosis, hypotension, hypertension, angioma, hypothermia, localized extreme cold, thromboembolism, compression of a blood vessel, rupture of a blood vessel, compression of a nerve, embolism, Sickle cell disease, inflammatory processes, hemorrhage, cardiac failure, cardiac arrest, shock, or anemia.

In certain embodiments, the subject is one in need of increased angiogenesis and/or arteriogenesis. For example, the subject may be one that has experienced ischemia, is currently experiencing ischemia, or has a disorder or condition that is likely to lead to an ischemic event such as an infarct or to chronic ischemia in a tissue. For example, the ischemia may be in a part of the body that is more susceptible to ischemia in diseases like diabetes, such as a limb, for example, a lower limb, for example, the foot and/or toes. In certain embodiments, the subject is at risk for ischemia, for example, a subject having a disease that predisposes the subject to ischemia. In one embodiment, the subject has diabetes (for example, type I or type II) or a pre-diabetic condition. The subject may be suffering from or at risk for one or more complications due to diabetes, such as nephropathy, retinopathy, coronary artery disease, peripheral vascular disease and associated ulcers, gangrene, and/or pain, and/or autonomic dysfunction. In other embodiments, the subject does not have diabetes (for example, type I or type II). In other embodiments, the subject has cardiovascular or cerebrovascular disease or has experienced ischemia or stroke. In other embodiments, the subject has a graft (for example, a skin graft) or other transplanted tissue, an anastomosis, a wound, an ulcer, a burn, male pattern baldness, atherosclerosis, ischemic heart tissue, ischemic peripheral tissue (for example, limb or mesentery ischemia), myocardial or cerebral infarction, or vascular occlusion or stenosis.

In some embodiments, the subject in need suffers from neovascular lesions. As described herein, a lesion is a region in an organ or tissue that has suffered damage through injury or disease. A neovascular lesion is a lesion associated with the formation of new blood vessels. Neovascular lesions are common in the choroid of the retina, including subfoveal neovascular lesions. Thus, in some embodiments provided herein is a method of repairing a choroidal neovascular lesion. Other neovascular lesions may also be repaired using the methods provided herein.

Routes of administering the isolated population of Treg cells include, but are not limited to, intravenous, intramuscular, subcutaneous, intraarticular, oral, topical, intradermal, transdermal, subdermal, parenteral, rectal, spinal, or epidermal administration. In some embodiments, administering Treg cells includes intramuscular, subcutaneous, or intravenous administration. In some embodiments, the Treg cells are administered in combination with a pharmaceutically acceptable carrier suited for the mode of administration. In some embodiments, Treg cells are administered in an amount of about $1\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, or $9\times10^7$ cells per administration, or an amount within a range defined by any two of the aforementioned values. In some embodiments, Tregs are administered in a single injection. In some embodiments, Tregs are administered in multiple dosages throughout a treatment period. In some embodiment, the isolated population of Treg cells is administered several times daily, twice daily, once daily, once weekly, once monthly, once quarterly, or once yearly, or at a frequency between any of the aforementioned periods.

As used herein, a "treatment period" is a length of time during which treatment is desirable. A treatment period could include an amount of time including 1, 2, 3, 4, 5, 6, or 7 days or 1, 2 3, 4, 5, 6, 7, or 8 weeks, or 1, 2, 3, 4, 5, 6, 7, 8, 9, 10, 11, or 12 months, or 1, 2, 3, 4, 5, 6, 7, 8, 9, 10, 11, 12, 13, 14, 15, 16, 17, 18, 19, or 20 years, or a period of time within a range defined by any two of the aforementioned amounts of time.

In some embodiments, a pharmaceutically acceptable carrier for injection can include, but is not limited to sterile water for injection and normal saline. Pharmaceutically acceptable carriers can contain a physiologically acceptable compound that acts to, for example, stabilize, or increase or decrease the absorption or clearance rates of the pharmaceutical compositions of the invention. Physiologically acceptable compounds can include, for example, carbohydrates, such as glucose, sucrose, or dextran, antioxidants, such as ascorbic acid or glutathione, chelating agents, low molecular weight proteins, detergents, liposomal carriers, or excipients or other stabilizers and/or buffers. Other physiologically acceptable compounds include wetting agents, emulsifying agents, dispersing agents or preservatives. See the 21st edition of Remington's Pharmaceutical Science, Mack Publishing Company, Easton, Pa. ("Remington's").

The pharmaceutical compositions of the present invention can also include ancillary substances, such as pharmacological agents, cytokines, or other biological response modifiers.

"Treatment," "treat," "treating," or "therapy" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, for example, arresting its development; (c) relieving and or ameliorating the disease or condition, for example, causing regression of the disease or condition; or (d) curing the disease or condition, for example, stopping its development or progression. The population of subjects treated by the methods of the invention includes subjects suffering from the undesirable condition or disease, as well as subjects at risk for development of the condition or disease.

Cord blood is a source of cells with enhanced regenerative capacities as compared to peripheral blood cell sources. Previous studies have demonstrated clinical proof of concept of expandability of cord blood Treg cells, as well as ability to use in an allogeneic manner (Brunstein, C. G., et al., Blood, 2011. 117(3): p. 1061-70). Accordingly, the possibility of cord blood Treg cells stimulating angiogenesis offers a potential means of stimulating a variety of therapeutic activities simultaneously. Thus, in some embodiments provided herein are methods and systems using cord blood cells purified for CD4 and CD25 expression that are capable of stimulating proliferation of blood vessel cells in vitro and in vivo. Also provided herein are methods and systems including CTLA-4 on the Treg cells to impart proliferative activity on endothelial cells.

The invention provides means of utilizing T regulatory cells for stimulation of angiogenesis in ischemic tissue. Using Treg cells for stimulating angiogenesis goes against conventional teachings, because Treg cells stimulate TGF-β, which is known to inhibit angiogenesis. However, in some embodiments, methods and systems of using Treg cells for stimulating angiogenesis are described. In one embodiment the invention teaches the use of non-matched cord blood derived T regulatory cells for treatment of ischemic conditions. The present invention includes compositions and methods for expanding T regulatory cells (Tregs), natural T regulatory cells (nTregs) for use in stimulation of angiogenesis. More preferably, the expanded cells retain nTreg or Treg phenotype and angiogenic activity following expansion.

The invention provides compositions and methods for expanding Tregs, preferably nTregs, without the subsequent reversion of the nTregs to T effector cells. Accordingly, such an expansion methodology allows for the establishment of a cell bank useful for stimulation of angiogenesis. In one aspect of the present invention, nTreg expansion can be performed by isolating nTregs from a desired cell source and subsequently culture expanding the cells in the presence of a primary signal and a co-stimulatory signal. Agents useful for stimulating a primary signal and an a co-stimulatory signal on Tregs may be used in soluble form, attached to the surface of a cell, or immobilized on a surface as described herein. In a preferred embodiment both primary and co-stimulatory agents are co-immobilized on a surface, for example a bead or an engineered cell. In one embodiment, the molecule providing the primary activation signal, such as a CD3 ligand, and the co-stimulatory molecule, such as a CD28 ligand are coupled to or loaded on the same surface, for example, a particle or an engineered cell. Said cells can be administered alone or with angiogenic cells to treat ischemic disorders.

In another embodiment, the invention provides a method of expanding Tregs, preferably nTregs to unprecedented numbers using a repetitive stimulation procedure. In one embodiment, the method of expanding nTregs includes restimulating nTregs based upon cell size. Preferably, nTregs exhibiting a cell size about the size of a resting nTreg are chosen for restimulation. In some instances, the size of a resting nTreg is about 8.5 µm. That is, the invention is based on the discovery that cell size is a parameter that contributes to the success of expanding nTregs without losing nTreg phenotype and suppressor activity. In another embodiment, the method of expanding nTregs includes restimulating nTregs in the presence of Rapamycin. Preferably, nTregs isolated from peripheral blood is re-stimulated in the presence of Rapamycin. That is, the invention is based on the discovery that Rapamycin contributes to the success of expanding nTregs isolated from peripheral blood without losing nTreg phenotype and suppressor activity. Preferably, the expanded cells of the invention maintain Foxp3 profile indicative of nTregs. In one embodiment, the population of expanded nTregs expresses specific natural Treg markers such as Foxp3 and Latency Associated Peptide (LAP), displayed Treg specific demethylation in the Foxp3 gene, and contain very few IL-2, IFNγ, IL-17 secreting cells. The expanded cells of the invention also are able to suppress limb loss in a xenogenic model of critical limb ischemia. In other embodiments, at least a portion of the active cell population is stored for later implantation/infusion. The population may be divided into more than one aliquot or unit such that part of the population of nTregs is retained for later application while part is applied immediately to the patient. Moderate to long-term storage of all or part of the cells in a cell bank is also within the scope of this invention. For the purpose of the invention, Treg and nTreg may be interchangeable.

EXAMPLES

Additional alternatives are disclosed in further detail in the following examples, which are not in any way intended to limit the scope of the claims.

General Procedures and Methods

Cord Blood Treg Cells

Cryopreserved cord blood units were provided under Regenerative Medicine Institute Institutional Review Board (IRB)-approved protocols. Cryopreserved human CB units were thawed and washed in CLINIMACS®, a wash buffer (Miltenyi Biotec, Bergish Gladbach, Germany) containing 0.5% HSA (Baxter Healthcare, Westlake Village, Calif.) to yield CB mononuclear cells (MNC). CB MNC were then subjected to CD25 cell enrichment using magnetic activated cell sorting (MACS) according to manufacturer's instructions (Miltenyi Biotec, Bergish Gladbach, Germany). Positively selected cells were co-cultured with CD3/28 co-expressing DYNABEADS®, magnetic separation beads (ClinExVivo™ CD3/CD28, Invitrogen Dynal AS, Oslo, Norway) at the indicated ratios and re-suspended at $1 \times 10^6$ cells/mL in XVIVO 15 medium (Cambrex BioScience, Walkersville, Md.) supplemented with 10% human AB serum (Gemini Bio-Products, Sacramento, Calif.), 2 mM L-glutamine (Sigma, St. Louis).

Co-Culture Assay

Human umbilical vein endothelial cells (HUVECs) were purchased from Cambrex (San Diego, Calif.) and were maintained in medium 199 (Mediatech, Inc, Herndon, Va.) containing 90 µg/mL heparin, 30 µg/mL endothelial cell growth supplements (BD Biosciences, Bedford, Mass.), 20% FBS, 50 µg/mL gentamicin, and 50 µg/mL amphotericin. Cultures were maintained at 37° C. in a humidified incubator (95% air, 5% CO2). HUVECs grown to 90% confluence on 6-well plates ($1 \times 10^6$ cells per well) were washed 3 times with PBS and cultured in serum-free medium for 24 hours for synchronization according to method previously described (He, S., et al., Arterioscler Thromb Vasc Biol, 2010. 30(12): p. 2621-30). Non-adherent cells were removed and culture medium was changed. For co-culture experiments, HUVECs were cultured without T cells, with Tregs (CD25$^+$), or with CD4$^+$CD25$^-$ T cells (CD25$^-$) for 48 hours in the presence of anti-CD3/anti-CD28 DYNABEADS®, magnetic separation beads at the indicated ratios with 200 IU/mL IL-2. Blocking experiments were performed using anti-CTLA4, anti-PD1, and anti-VEGF antibodies. Proliferation was assessed by removing T cells (non-adherent), washing cells, purifying T cells using a CD3 T cell column (R&D Systems), counting, and subsequently replating in the presence of 1 uC/well tritiated thymidine. Proliferation was assessed by scintillation counting and expressed as counts per minute (CPM).

Treg Expansion Assay

T-175 flasks were coated with human Wharton's Jelly MSC and allowed to proliferate until 75% confluence, at which point Treg or Tcon were added to the culture. In some cultures the same cocktail used to expand Tregs described above was utilized. Cells were passaged every week and subsequently harvested.

Hindlimb Ischemia Assay

All procedures involving mice were carried out according to NIH recommended procedures and precautions. Mice were housed under standard room conditions, with ad libidum food and water. Every effort was made to minimize animal suffering. BALB/c mice were treated by femoral artery ligation and local nerve injury in a previously published model (Meng et al., 2007, J. Trans. Med. 5:57).

Example 1: HUVEC Activation with Umbilical Cord Blood

Previous studies have demonstrated that peripheral blood derived Treg cells inhibit inflammatory marker expression from HUVEC cells, however, effects of Treg cells on proliferation of HUVEC cells has not been assessed to our knowledge. Accordingly, we examined proliferation of HUVEC cells cultured with various concentrations of cord blood Treg cells. Furthermore in order to assess whether activation status of Treg cells affected HUVEC stimulating activity, both freshly isolated, and IL-2, CD3/CD28 DYNABEADS®, magnetic separation beads were assessed for HUVEC stimulatory activity. As seen in FIG. 1, upregulation of HUVEC proliferation was observed in a dose-dependent manner after co-culture with activated Treg but not nave Treg. Furthermore, neither nave CD4$^+$Foxp3$^-$ T cells (Tcon), nor activated Tcon were able to stimulate HUVEC cell proliferation. To ensure that proliferation was mediated by T cells, T cells were washed off HUVEC before pulsing with tritiated thymidine for assessment of proliferation.

Figure 2:
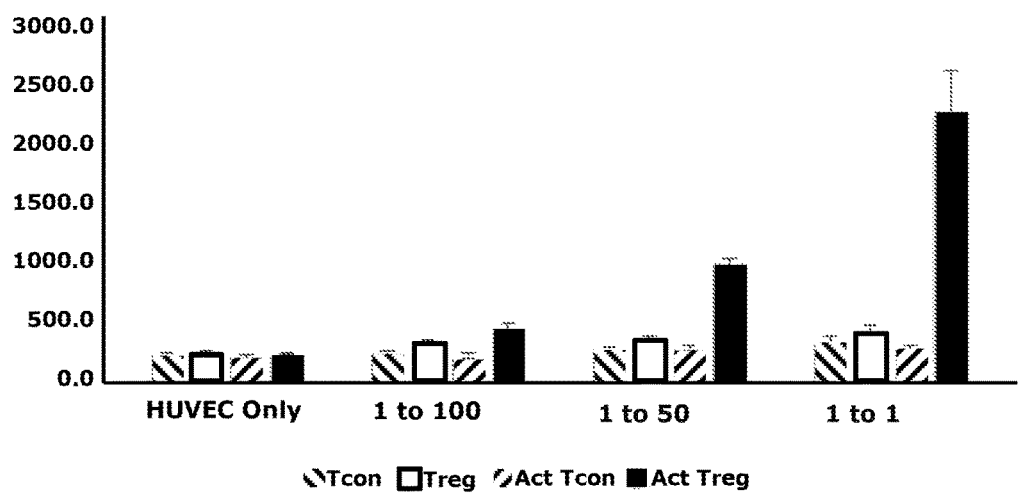
FIG. 2 illustrates the results of stimulation of vascular endothelial growth factor (VEGF) production by activated Treg cells in an embodiment described herein.
Figure 3:
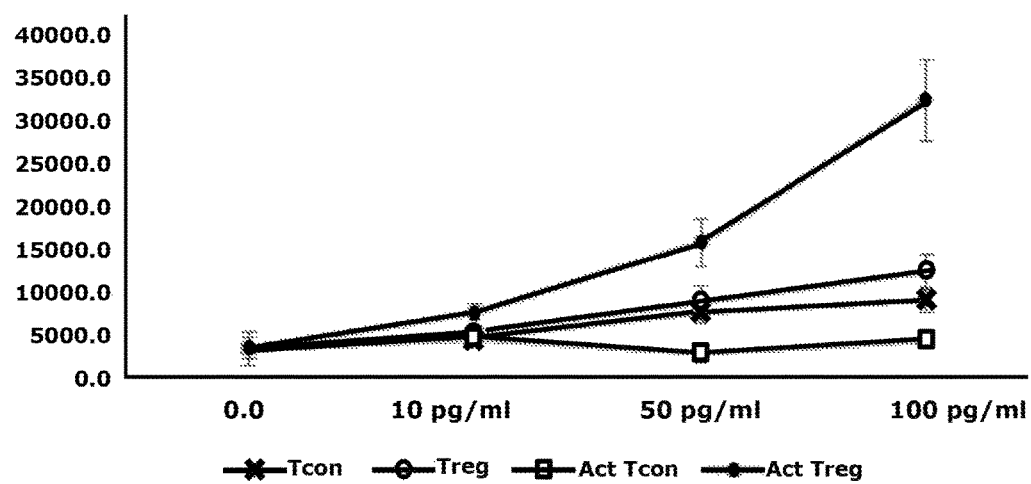
FIG. 3 illustrates the results of Treg cell-induced hypersensitivity to VEGF stimulated proliferation in an embodiment described herein.
Figure 4:
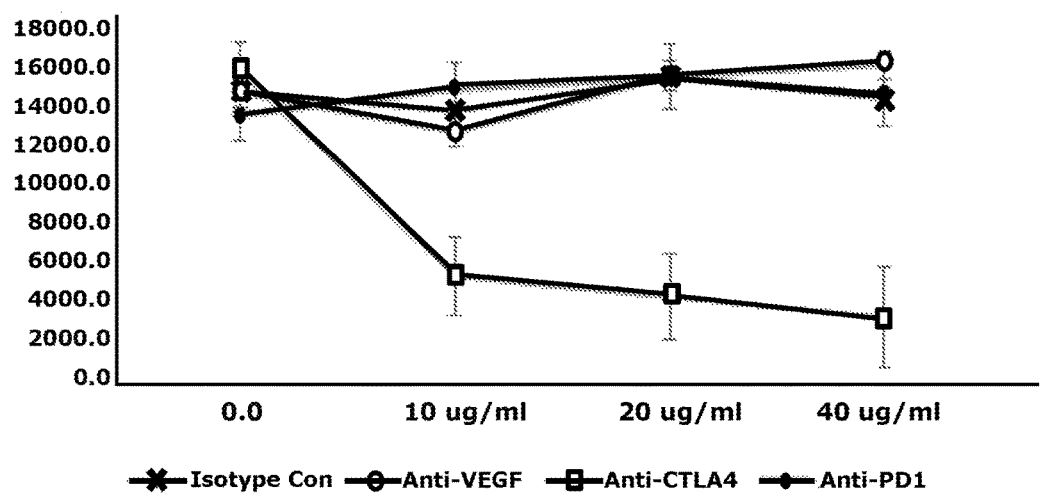
FIG. 4 illustrates the results of inhibition of Treg stimulation of HUVEC proliferation by CTLA-4 in an embodiment described herein.

VEGF is a well-known marker of angiogenesis, playing a fundamental role in different cellular activities which culminate in formation of new blood vessels (Gianni-Barrera, R., et al., Biochem Soc Trans, 2014. 42(6): p. 1637-42). In order to assess whether HUVEC proliferation was associated with angiogenic activity, assessment of VEGF production by HUVEC was measured in response to culture with Treg. While VEGF is typically considered a stimulator of HUVEC proliferation, autocrine VEGF has been shown in HUVEC cells, which is believed to play a role in their structural integrity. Furthermore activation of HUVEC has been demonstrated to induce upregulation of VEGF production (Gianni-Barrera, R., et al., Biochem Soc Trans, 2014. 42(6): p. 1637-42). As shown in FIG. 2, stimulation of VEGF production was observed by treatment of HUVEC with activated cord blood Treg but not control cells. Furthermore, VEGF induced HUVEC proliferation was stimulated by coculture with activated cord blood Treg but not control cells (FIG. 3). In order to assess whether molecular signals associated with T cell biological activities affect Treg stimulation of HUVEC proliferation, addition of antibodies to CTLA-4, PD-1, and VEGF was performed in cultures of 1:1 Treg to HUVEC. Interestingly, only anti-CTLA4 antibody was capable of dose-dependently inhibiting spontaneous, and VEGF-stimulated proliferation of HUVEC cells (FIG. 4).

This example demonstrates that in some embodiments, T regulatory cells induce angiogenesis. In some embodiments, Treg cells in an activated state are capable of stimulating HUVEC proliferation, VEGF production, and responsiveness to VEGF.

Example 2: Isolation of Stromal Vascular Fraction Cells

The following example demonstrates an example of isolating stromal vascular fraction cells.

Using aseptic techniques and with local anesthesia, the infraumbilical region is infiltrated with 0.5% xylocaine with 1:200,000 epinephrine. Following 10 minutes for hemostasis, a 4 mm cannula attached to a 60 cc Toomey syringe is used to aspirate 500 cc of adipose tissue in a circumcisional radiating technique. As each of 9 syringes is filled, the syringes are removed from the cannula, capped, and exchanged for a fresh syringe in a sterile manner within the sterile field. Using aseptic laboratory techniques, the syringe-filled lipoaspirate is placed into two sterile 500 mL centrifuge containers and washed three times with sterile Dulbecco's phosphate-buffered saline to eliminate erythrocytes. ClyZyme/PBS (7 mL/500 mL) is added to the washed lipoaspirate using a 1:1 volume ratio. The centrifuge containers are sealed and placed in a 37° C. shaking water bath for one hour, then centrifuged for 5 min at 300 rcf. Following centrifugation, the stromal cells are resuspended within the isolyte in separate sterile 50 mL centrifuge tubes. The tubes are centrifuged for 5 min. at 300 rcf and the isolyte is removed, leaving cell pellet. The pellets are resuspended in 40 mL of isolyte, centrifuged again for 5 min at 300 rcf. The supernatant is again removed, and the cell pellets are combined and filtered through 100 µm cell strainers into a sterile 50 mL centrifuge tube and centrifuged for 5 min at 300 rcf and the supernatant removed, leaving the pelleted adipose stromal cells.

Example 3: Culture and Expansion of T Regulatory Cells

Cryopreserved cord blood bags (1 unit bags) were thawed and washed in CLINIMACS®, a wash buffer (Miltenyi Biotec, Bergish Gladbach, Germany) containing 0.5% HSA (Baxter Healthcare, Westlake Village, Calif.) in order to purify mononuclear cells. Subsequently, cells $CD25^+$ cell enrichment was performed by positive selection using magnetic activated cell sorting (MACS) according to manufacturer's instructions (Miltenyi Biotec, Bergish Gladbach, Germany). Cells were check for viability and subsequently stimulated by co-cultured with CD3/28 co-expressing DYNABEADS®, magnetic separation beads (ClinExVivo™ CD3/CD28, Invitrogen Dynal AS, Oslo, Norway) at a 1:3 cell to bead ratio and re-suspended at $1 \times 10^6$ cells/mL in X-VIVO 15 medium (Cambrex BioScience, Walkersville, Md.) supplemented with 10% human AB serum (Gemini Bio-Products, Sacramento, Calif.), 2 mM L-glutamine (Sigma, St. Louis, Mo.), 1% Penicillin-Streptomycin (Gibco/Invitrogen, Grand Island, N.Y.)] and 200 IU/mL interleukin (IL)-2 (CHIRON Corporation, Emeryville, Calif.). Ex vivo co-culture of the $CD25^+$ cells and beads was performed in tissue culture flasks at 37° C. in a 5% $CO_2$-in-air atmosphere. The CB-derived $CD25^+$ enriched T-cells were maintained at $1 \times 10^6$ cells/mL by the addition of fresh medium and IL-2 (maintaining 200 IU/mL) every 48-72 hours. An addition of Wharton's Jelly MSC was performed in some cultures. Said MSC were pre-plated at 50% confluency prior to addition of cord blood cells as described above.

Example 4: Enhanced Treg Cell Expansion Co-Cultured with MSC Feeder Layers

Previous studies have demonstrated that mesenchymal stem cells (MSC) are capable of producing growth factors associated with cellular proliferation such as FGF (Lai, W. T., V. Krishnappa, and D. G. Phinney, Stem Cells, 2011. 29(7): p. 1102-11; Coutu, D. L., M. Francois, and J. Galipeau, Blood, 2011. 117(25): p. 6801-12), VEGF (Kinnaird, T., et al., Circulation, 2004. 109(12): p. 1543-9; Kinnaird, T., et al., Circ Res, 2004. 94(5): p. 678-85; Kwon, H. M., et al., Vascul Pharmacol, 2014. 63(1): p. 19-28), IGF-1 (Montes, R., et al., Cell Res, 2009. 19(6): p. 698-709) and HGF (Shen, C., et al., Mol Med Rep, 2015. 12(1): p. 20-30). In fact MSC feeder layers have previously been used to expand hematopoietic (Walenda, T., et al., Exp Hematol, 2011. 39(6): p. 617-28; Fong, C. Y., et al., J Cell Biochem, 2012. 113(2): p. 658-68), and pluripotent stem cells (Zou, Q., et al., PLoS One, 2016. 11(2): p. e0149023; Silva Dos Santos, D., et al., Cell Med, 2014. 7(1): p. 25-35) while maintaining these cells in an undifferentiated state.

Figure 5:
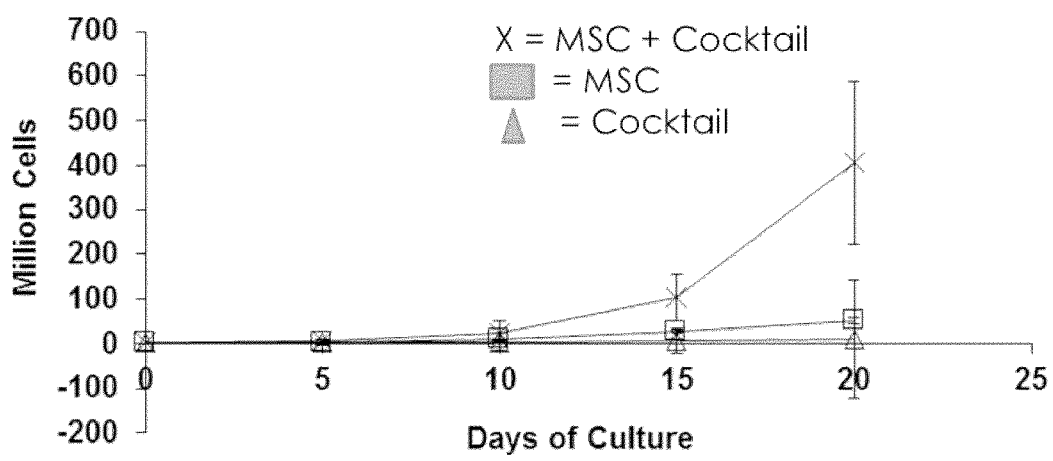
FIG. 5 illustrates the results of expansion of umbilical cord derived Treg enhanced by co-culture with mesenchymal stem cell (MSC) feeder layers in an embodiment described herein.
Figure 6:
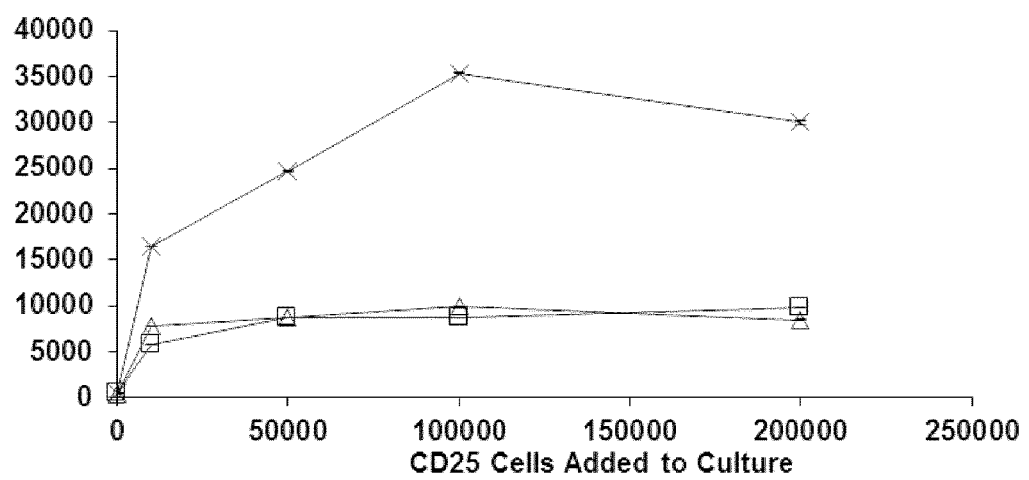
FIG. 6 illustrates the increased ability to stimulate proliferation of HUVEC cells with culture expanded Treg when combined with MSC feeder layers as described in an embodiment herein.

Furthermore, MSC have been demonstrated to promote generation of Treg cells in vitro (Cahill, E. F., et al., Stem Cell Res Ther, 2015. 6: p. 19; Wang, Z. X., et al., Mol Cell Biochem, 2015. 400(1-2): p. 163-72; Kwon, M. S., et al., J Neurochem, 2014. 131(2): p. 206-18; Luz-Crawford, P., et al., Stem Cell Res Ther, 2013. 4(3): p. 65; Erkers, T., et al., Stem Cells Dev, 2013. 22(19): p. 2596-605; Engela, A. U., et al., Clin Exp Immunol, 2013. 173(2): p. 343-54), and in vivo (Bai, L., et al., Nat Neurosci, 2012. 15(6): p. 862-70; Lee, E. S., et al., PLoS One, 2015. 10(9): p. e0138846; Treacy, O., et al., Am J Transplant, 2014. 14(9): p. 2023-36). When purified $CD4^+CD25^+$ cells were added to standard CD3 CD28 beads with IL-2 supplementation increased cell number in tissue culture was 50,000 cells at input and 50 million cells after 20 days of culture. In contrast, culture on Wharton's Jelly feeder cells resulted in 5 million cells generated from 50,000 cells at input after the same culture period (FIG. 5). Ability to stimulate proliferation of HUVEC cells was significantly increased with culture expanded Treg when the combination of cocktail and MSC feeders was used (FIG. 6).

Example 5: Stimulation of Angiogenesis in Vitro

Treg cells generated as in Example 3 were added at the indicated concentration to HUVEC cells and proliferation was assessed by tritiated thymidine after 48 hours of culture.

Figure 7:
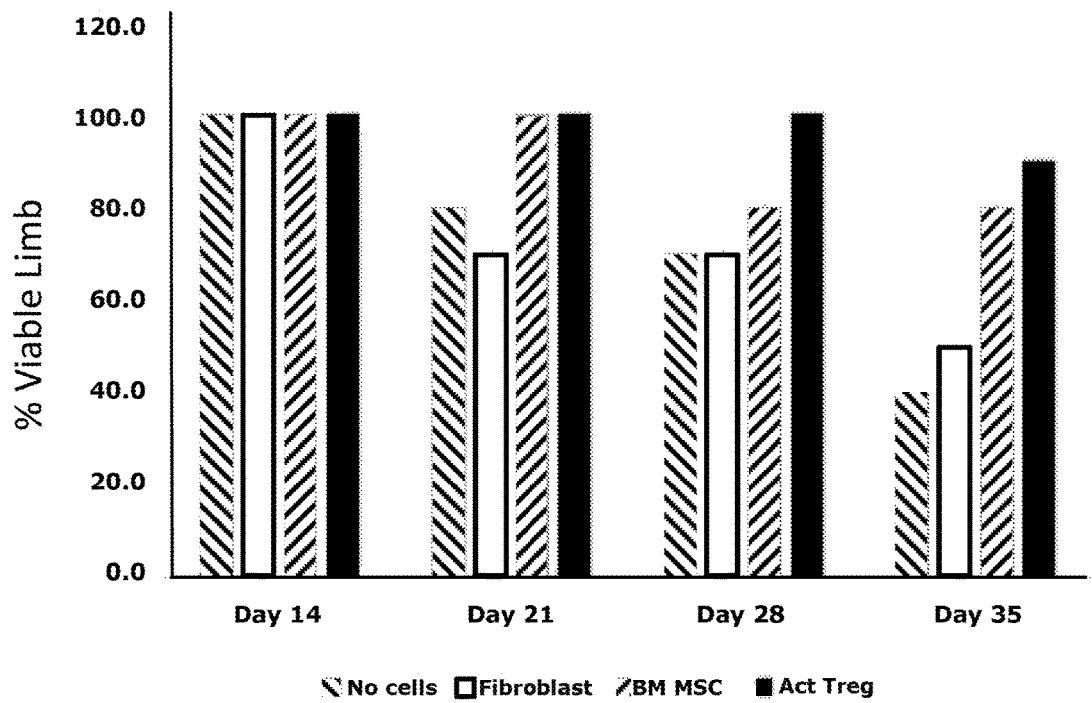
FIG. 7 depicts the results of protection from limb loss by cord blood expanded Treg cells in an embodiment described herein.

Example 6: Protection from Limb Loss by Administration of Cord Blood Expanded Treg Cells Previous studies have demonstrated that bone marrow mesenchymal stem cells (MSC) are capable of restoring circulation in the hindlimb ischemia model subsequent to intramuscular administration of cells through inducing formation of collateral blood vessels (Hoffmann, J., et al., Thorac Cardiovasc Surg, 2010. 58(3): p. 136-42; Iwase, T., et al., Cardiovasc Res, 2005. 66(3): p. 543-51). Accordingly, we sought to determine whether expanded Treg cells possessed ability to induce similar therapeutic angiogenesis. Given that cord blood expanded Treg cells are of human origin, control human fibroblasts were utilized. Additionally, syngeneic mouse bone marrow was used as a positive control. As seen in FIG. 7, a profound reduction in limb loss was obtained with expanded.

Example 7: Stimulation of Angiogenesis In Vivo

BALB/c mice were treated by femoral artery ligation and local nerve injury in a previously published model (Meng et al., 2007, J. Trans. Med. 5:57). Treg generated as in Example 3 were injected at a concentration of 2 million cells intramuscularly on day 3 post injury. The limb loss was substantially less as compared to control treated mice. The two tables below represent independent experiments.

TABLE 1

| Mouse Number | Day 7 | Day 14 | Day 21 | Day 28 | Day 35 |
|---|---|---|---|---|---|
| 1 Control | | | Limb Loss | | |
| 2 Control | | | Limb Loss | | |
| 3 Control | | | | Limb Loss | |
| 4 Control | | | Limb Loss | | |
| 5 Control | | | | Limb Loss | |
| 6 Control | | | | Limb Loss | |
| 7 Control | | | | Limb Loss | |
| 8 Treated | | | | | |
| 9 Treated | | | | | |
| 10 Treated | | | | | Limb Loss |
| 11 Treated | | | | | |
| 12 Treated | | | | | |
| 13 Treated | | | | | |
| 14 Treated | | | | | Limb Loss |

TABLE 2

| Mouse Number | Day 7 | Day 14 | Day 21 | Day 28 | Day 35 |
|---|---|---|---|---|---|
| 1 Control | | | Limb Loss | | |
| 2 Control | | | | Limb Loss | |
| 3 Control | | | Limb Loss | | |
| 4 Control | | Limb Loss | | | |
| 5 Control | | | Limb Loss | | |
| 6 Control | | | Limb Loss | | |
| 7 Control | | | Limb Loss | | |
| 8 Treated | | | | | |
| 9 Treated | | | | | |
| 10 Treated | | | | | |
| 11 Treated | | | | | |
| 12 Treated | | | | | |
| 13 Treated | | | | | |
| 14 Treated | | | | | |

These examples demonstrate that in some embodiments, in vivo activated Treg cells stimulate angiogenesis. In some embodiments, blockade of CTLA-4 induces a dose-dependent inhibition of proliferation. CTLA-4 has previously been shown to induce alterations in antigen presenting cells, such as induction of indolamine 2,3 deoxygenase production via a CD80/CD86 "outside-in" signaling (Onodera, T., et al., J Immunol, 2009. 183(9): p. 5608-14; Fallarino, F., et al., Nat Immunol, 2003. 4(12): p. 1206-12).

Example 8: Stimulation of Angiogenesis in Humans

The activated Treg cells described herein can be used to enhance and stimulate angiogenesis in a human subject.

Human subjects identified as having ischemia are selected for participation in this study. Activated Treg cells generated as in Example 3 are transplanted to the human subjects by any suitable delivery method. For example, cells are administered directly to a target site (such as a limb, myocardium, or brain) by injection of cells in a suitable carrier or diluent, or by surgical delivery to an internal or external target site, or by a catheter to a site accessible by a blood vessel. Some modes of injection include intramuscular injection. For exact placement, cells may be precisely delivered into a site using stereotactic injection techniques.

The cells are administered to the subject in an effective amount, that is, in an amount capable of producing a desirable result in the treated subject, for example, by enhancing angiogenesis. Such therapeutically effective amounts may be determined empirically. The range may vary considerably based on the subject age or size, and based on the severity of the condition. In general, the cells may be administered in an amount ranging from about $10^4$-$10^7$ cells, including $1\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, or $9\times10^7$ cells per administration, or an amount within a range defined by any two of the aforementioned values. In some embodiments, Tregs are administered in a single injection. In some embodiments, Tregs are administered in multiple dosages throughout a treatment period. In some embodiment, the isolated population of Treg cells is administered several times daily, once daily, once weekly, once monthly, once quarterly, or once yearly, or at a frequency between any of the aforementioned periods.

The cells may be administered to the subject in any suitable formulation or composition. Compositions or formulations may be administered to the subject alone or in combination with pharmaceutically acceptable carriers in a manner selected on the basis of mode and route of administration. A description of exemplary pharmaceutically acceptable carriers and diluents, as well as pharmaceutical formulations, can be found in Remington's Pharmaceutical Sciences. Other substances may be added to the compositions to stabilize and/or preserve the compositions.

Upon administration of the composition, the subject can be evaluated to determine efficacy of the composition, for determining the propriety of providing additional doses. Indicators of improved or enhanced angiogenesis include a measure and pacing of cardiac beats, a measure of the growth of new blood vessels, a measure of improved blood flow to a certain region or tissue, or a measure of tissue health and appearance.

Example 9: Repairing Neovascular Lesion

The activated Treg cells disclosed herein may be used for the repair of neovascular lesions. In some patients in need, retinal pigmented epithelial (RPE) cells surround a neovascular lesions associated with neovascular age-related macular degeneration (AMD) and is associated with reduced edema, reduced choroidal neovascularization (CNV), and reduced growth of CNV lesions. This wound healing process mediated by RPE cells seals off the neovascular lesion to reform an intact RPE layer separating the retina from the invading choroidal blood vessels. Once the RPE has reformed an intact layer, the neovascular lesion is stabilized. Thus, administration of activated Treg cells to these patients can promote the RPE layer at the site of the neovascular lesion and thereby promote wound healing to more effectively seal off the neovascular lesion and reduce the need for anti-neovascular treatment. While not intending to be bound by any particular theory or mechanism of action, it is believed that treatment with activated Treg cells can lead to the production of a larger proportion of RPE cells surviving the inflammatory insult which occurs in the neovascular lesion, enhancement of the normal RPE phenotype which migrates to the site to seal the lesion; stabilization of the RPE phenotype, and inhibition of the differentiation of the RPE into undesirable cell types such as fibroblasts. Activated Treg cells may be administered by intraocular injections (including for example, intravitreal, subretinal, intraanterior chamber, intrascleral) or periocular (including, for example, topical application to the cornea, subconjunctival, subtenon, or transcleral). The cells may be administered in an amount ranging from about $10^4$-$10^7$ cells, including $1\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, or $9\times10^7$ cells per administration, or an amount within a range defined by any two of the aforementioned values. In some embodiments, Tregs are administered in a single injection. In some embodiments, Tregs are administered in multiple dosages throughout a treatment period. In some embodiment, the isolated population of Treg cells is administered several times daily, once daily, once weekly, once monthly, once quarterly, or once yearly, or at a frequency between any of the aforementioned periods. The compositions may be formulated with the appropriate pharmaceutically acceptable carriers and diluents according to the mode and route of administration.

Other forms of neovascular lesions, not associated with the retina may also be repaired by administration of the activated Treg cells in a similar manner, where activated Treg cells are administered to the site of the neovascular lesion. The activated Treg cells may be administered by any acceptable route, including intramuscular injection or surgical transplant directly to the site of the lesion. The activated Treg cells may be administered in an amount ranging from about $10^4$-$10^7$ cells, including $1\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, or $9\times10^7$ cells per administration, or an amount within a range defined by any two of the aforementioned values. In some embodiments, Tregs are administered in a single injection. In some embodiments, Tregs are administered in multiple dosages throughout a treatment period. In some embodiments, the isolated population of Treg cells is administered several times daily, once daily, once weekly, once monthly, once quarterly, or once yearly, or at a frequency between any of the aforementioned periods.

Example 10: Critical Limb Ischemia

Five patients suffering from critical limb ischemia were recruited. Patients matched the following inclusion criteria: a) Unreconstructable arterial disease will be determined by a vascular surgeon who is not participating in the study. Unreconstructable arterial disease is defined by atherocclusive lesions within the arterial tree of the extremity that due to extent or morphology are not amenable to surgical bypass or PTCA and stenting; b) Objective evidence of severe peripheral arterial disease will include an ankle brachial index (ABI) of less than 0.55, and/or a resting toe brachial index (TBI) of less than 40; c) Patients must be competent to give consent; and d) No history of malignant disease except for nonmelanoma skin cancer, no suspicious findings on chest x-ray, mammography (women over age 35), Papanicolaou smear (women over age 40), a normal fecal occult blood (over age 50) and a normal prostate specific antigen (men over age 45).

Patients were injected with 10(8) cord blood expanded T regulatory cells generated as described in above example. Injections were performed using 10 million cells per injection, with 10 injections locally at the area of failed perfusion in a 10 cm×10 cm area in the gastrocnemius muscle. Ankle Brachial index was measured by comparing the ankle and brachial pressure. No patients reported amputation during the study period.

| Patient Number | Pre | 1 month | 3 month | 6 month |
|---|---|---|---|---|
| Improvements in Ankle Brachial Index | | | | |
| 1 | .55 | .75 | .83 | .88 |
| 2 | .49 | .61 | .64 | .55 |
| 3 | .59 | .62 | .89 | .59 |
| 4 | .43 | .88 | .84 | .79 |
| 5 | .48 | .64 | .77 | .89 |
| Improvements in Ankle Pressure (mmHg) | | | | |
| 1 | 63 | 73 | 78 | 81 |
| 2 | 71 | 65 | 63 | 59 |
| 3 | 63 | 59 | 78 | 64 |
| 4 | 55 | 71 | 75 | 83 |
| 5 | 51 | 58 | 85 | 84 |

Embodiments

Some aspects described herein further relate to the following numbered embodiments.

1. A method of stimulating angiogenesis comprising the steps of: a) obtaining a population of cells containing T regulatory cells; b) selecting said T regulatory cells from said population of cells; c) activating said T regulatory cells to enhance angiogenic activity of said T regulatory cells; and d) administering said T regulatory cells in a patient in need of therapy.

2. The method of embodiment 1, wherein said population of cells containing T regulatory cells is peripheral blood mononuclear cells.

3. The method of embodiment 1, wherein said population of cells containing T regulatory cells is mobilized peripheral blood mononuclear cells.

4. The method of embodiment 3, wherein said mobilization is achieved by administration of G-CSF.

5. The method of embodiment 3, wherein said mobilization is achieved by administration of flt-3 ligand.

6. The method of embodiment 3, wherein said mobilization is achieved by administration of thrombopoietin.

7. The method of embodiment 3, wherein said mobilization is achieved by administration of Mozobil.

8. The method of embodiment 1, wherein said population of cells containing T regulatory cells is cord blood.

9. The method of embodiment 1, wherein said population of cells containing T regulatory cells is menstrual blood.

10. The method of embodiment 1, wherein said population of cells containing T regulatory cells is adipose derived stromal vascular fraction cells.

11. The method of embodiment 1, wherein said T regulatory cells possess ability to inhibit proliferation of naïve T cells stimulated with a signal that activates proliferation.

12. The method of embodiment 11, wherein said signal that activates proliferation is selected from a group comprising of: a) anti-CD3 and anti-CD28 beads; b) concanavalin A; c) PHA; and d) stimulation with alloreactive antigen presentation cells.

13. The method of embodiment 1, wherein said T regulatory cell is capable of suppressing maturation of dendritic cells.

14. The method of embodiment 13, wherein said maturation is dendritic cells is upregulation of molecules selected from a group comprising of: CD80; CD40; CD86; and HLA II.

15. The method of embodiment 1, wherein said T regulatory cell possesses expression of GITR ligand.

16. The method of embodiment 1, wherein said T regulatory cell expresses neuropilin-1.

17. The method of embodiment 1, wherein said T regulatory cell expresses CTLA-4.

18. The method of embodiment 1, wherein said T regulatory cell expresses CD25.

19. The method of embodiment 1, wherein said T regulatory cell expresses CD105.

20. The method of embodiment 1, wherein said T regulatory cell expresses membrane bound TGF-beta.

21. The method of embodiment 1, wherein said T regulatory cell produces IL-10.

22. The method of embodiment 1, wherein said T regulatory cells are activated by exposure to vasoactive intestinal peptide.

23. The method of embodiment 1, wherein said T regulatory cells are activated by exposure to IL-10

24. The method of embodiment 1, wherein said T regulatory cells are activated by exposure to TGF-beta 25. The method of embodiment 1, wherein said T regulatory cells are activated by exposure to mesenchymal stem cell conditioned media.

26. The method of embodiment 1, wherein said T regulatory cells are activated by exposure to mesenchymal stem cell derived exosomes.

27. The method of embodiment 1, wherein said T regulatory cells are activated by exposure to BDNF.

28. The method of embodiment 1, wherein said T regulatory cells are activated by exposure to human chorionic gonadotropin.

29. The method of embodiment 1, wherein said T regulatory cells are activated by exposure to VEGF.

30. The method of embodiment 1, wherein said T regulatory cells are activated by exposure to CD3 and CD28 antibodies.

31. The method of embodiment 1, wherein said T regulatory cells are anergic T cells.

32. The method of embodiment 1, wherein said T regulatory cells are activated by exposure to hypoxic conditions.

33. The method of embodiment 1, wherein said T regulatory cells are activated by exposure to angiopoietin.

34. The method of embodiment 1, wherein said T regulatory cells express FoxP3.

35. The method of embodiment 1, wherein said T regulatory cells express CD39.

36. The method of embodiment 1, wherein said T regulatory cells express CD73.

37. The method of embodiment 1, wherein said T regulatory cells express CD127.

38. The method of embodiment 1, wherein said T regulatory cells express GARP.

39. The method of embodiment 1, wherein said T regulatory cells are activated by exposure to rapamycin.

40. The method of embodiment 1, wherein said T regulatory cells are activated by culture with mesenchymal stem cells.

41. The method of embodiment 40, wherein said mesenchymal stem cells are obtained from a group of tissues comprised of: a) adipose; b) bone marrow; c) tooth pulp; d) hair follicle; e) endometrium; f) menstrual blood; g) peripheral blood; h) omentum; i) skin; j) cord blood; k) Wharton's jelly; l) placenta; and m) fallopian tube.

42. The method of embodiment 41, wherein said adipose derived mesenchymal stem cells are expanded purified mesenchymal stem cells possessing the markers: a) CD90; b) CD105 and c) CD73.

43. The method of embodiment 41, wherein said adipose derived mesenchymal stem cells are stromal vascular fraction cells.

44. The method of embodiment 43, wherein said stromal vascular fraction cells are isolated by the following steps:
using aseptic technique and with local anesthesia, the infraumbilical region is infiltrated with 0.5% Xylocaine with 1:200,000 epinephrine;
after allowing 10 minutes for hemostasis, a 4 mm cannula attached to a 60 cc Toomey syringe is used to aspirate 500 cc of adipose tissue in a circumcisional radiating technique;
as each of 9 syringes is filled, said syringes are removed from the cannula, capped, and exchanged for a fresh syringe in a sterile manner within the sterile field;
using aseptic laboratory technique, the syringe-filled lipoaspirate are placed into two sterile 500 mL centrifuge containers and washed three times with sterile Dulbecco's phosphate-buffered saline to eliminate erythrocytes;
ClyZyme/PBS (7 mL/500 mL) is added to the washed lipoaspirate using a 1:1 volume ratio;
the centrifuge containers are sealed and placed in a 37° C. shaking water bath for one hour then centrifuged for 5 min at 300 rcf;
following centrifugation, the stromal cells are resuspended within Isolyte in separate sterile 50 mL centrifuge tubes;
the tubes are centrifuged for 5 min. at 300 rcf and the Isolyte is removed, leaving cell pellet;
the pellets are resuspended in 40 mL of Isolyte, centrifuged again for 5 min at 300 rcf.
the supernatant is again removed;

the cell pellets are combined and filtered through 100 μm cell strainers into a sterile 50 mL centrifuge tube and centrifuged for 5 min at 300 rcf and the supernatant removed, leaving the pelleted adipose stromal cells.

45. The method of embodiment 41, wherein, wherein said adipose derived cells are positively selected for a marker chosen from a group comprising of: a) CD105; b) CD73; c) CD44; d) CD90; e) VEGFR2; and f) TEM-1.

46. The method of embodiment 45, wherein said adipose derived cells are negatively selected for markers chosen from a group comprising of: a) HLA-DR; b) CD45; and c) CD14.

47. The method of embodiment 41, wherein said bone marrow mesenchymal stem cells are selected for expression of the marker Stro-1.

48. The method of embodiment 41, wherein said bone marrow mesenchymal stem cells are selected for expression of the marker CD73.

49. The method of embodiment 41, wherein said bone marrow mesenchymal stem cells are selected for expression of the marker aldehyde dehydrogenase.

50. The method of embodiment 41, wherein said bone marrow mesenchymal stem cells are selected for ability to inhibit mixed lymphocyte reaction.

51. The method of embodiment 41, wherein said bone marrow mesenchymal stem cells express the marker NGF-receptor p75.

52. The method of embodiment 41, wherein said endometrial derived mesenchymal stem cells are endometrial regenerative cells.

53. A method of stimulating angiogenesis comprising administering a T regulatory cell into an ischemic tissue.

54. The method of embodiment 53, wherein said ischemic tissue is a limb of a patient suffering from peripheral artery disease.

55. The method of embodiment 53, wherein said ischemic tissue is a limb of a patient suffering from critical limb ischemia.

56. The method of embodiment 53, wherein said ischemic tissue is cardiac muscle of a patient suffering from coronary artery disease.

57. The method of embodiment 53, wherein said ischemic tissue is cardiac muscle of a patient suffering from heart disease.

58. The method of embodiment 53, wherein said T regulatory cell expresses the marker CD25.

59. The method of embodiment 53, wherein said T regulatory cell expresses the marker CTLA4.

60. The method of embodiment 53, wherein said T regulatory cell possesses the ability to inhibit proliferation of an activated T cell by more than 25% at a ratio of 1 T regulatory cell to 1 activated T cell.

61. The method of embodiment 53, wherein said T regulatory cell possesses ability to inhibit dendritic cell maturation.

62. The method of embodiment 61, wherein said dendritic cell maturation is defined as upregulation of CD80.

63. The method of embodiment 61, wherein said dendritic cell maturation is defined as upregulation of CD86.

64. The method of embodiment 61, wherein said dendritic cell maturation is defined as upregulation of CD40.

65. The method of embodiment 53, wherein said T regulatory cell is derived from cord blood.

66. The method of embodiment 53, wherein said T regulatory cell is derived from peripheral blood.

67. The method of embodiment 53, wherein said T regulatory cell is derived from menstrual blood.

68. The method of embodiment 53, wherein said T regulatory cell is derived from mobilized peripheral blood.

69. The method of embodiment 68, wherein said mobilization is achieved by administration of G-CSF.

70. The method of embodiment 68, wherein said mobilization is achieved by administration of Mozibil.

71. The method of embodiment 53, wherein said T regulatory cell is activated by agents that induce CD3 intracellular signaling.

72. The method of embodiment 53, wherein said T regulatory cell is activated rapamycin treatment.

73. The method of embodiment 53, wherein said T regulatory cell is activated by culture with anti-CD3 and anti-CD28 antibodies.

74. The method of embodiment 73, wherein said anti-CD3 and anti-CD28 antibodies are bound to a surface.

75. The method of embodiment 74, wherein said surface is a bead.

76. The method of embodiment 53, wherein said activation of said T regulatory cell is achieved by culture in a combination consisting of one or more agents from a group comprising of: a) IL-2; b) rapamycin; c) anti-CD3 antibody; and d) anti-CD28 antibody.

77. The method of embodiment 76 wherein mesenchymal stem cells are added to said culture.

78. A method of stimulating angiogenesis by administration of allogeneic T regulatory cells together with an angiogenic cell population.

79. The method of embodiment 78, wherein said angiogenic cell population is endothelial progenitor cells.

80. The method of embodiment 78, wherein said angiogenic cell population is mesenchymal stem cells.

81. The method of embodiment 78, wherein said angiogenic cell population is mesenchymal progenitor cells.

82. The method of embodiment 78, wherein said angiogenic cell population is peripheral blood mononuclear cells.

83. The method of embodiment 78, wherein said angiogenic cell population is bone marrow mononuclear cells.

84. The method of embodiment 78, wherein said angiogenic cell population is CD34 positive cells.

85. The method of embodiment 78, wherein said angiogenic cell population is CD133 positive cells.

While the inventions are susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims.

What is claimed is:

1. A method of stimulating VEGF-dependent angiogenesis in a subject having critical limb ischemia, the method comprising:
    obtaining a population of allogeneic cells comprising T regulatory cells;
    selecting said T regulatory cells from said population of allogeneic cells;
    activating said T regulatory cells, wherein activating said T regulatory cells comprises exposing said T regulatory cells to CD3 and CD28 antibodies; and
    administering said activated T regulatory cells to a subject having critical limb ischemia,
    wherein said administered activated T regulatory cells stimulate VEGF-dependent angiogenesis in said subject.

2. The method of claim 1, wherein said population of allogeneic cells comprising T regulatory cells comprises peripheral blood mononuclear cells.

3. The method of claim 1, wherein said activated T regulatory cells are administered in an amount of about $2 \times 10^6$ cells.

4. The method of claim 1, wherein stimulating VEGF-dependent angiogenesis treats critical limb ischemia in a subject.

5. The method of claim 1, wherein the activated T regulatory cells are administered by intramuscular injection in an amount of about 1-90 million cells per injection.

6. The method of claim 1, wherein said population of allogeneic cells comprising T regulatory cells comprises cord blood.

7. The method of claim 1, wherein said population of allogeneic cells comprising T regulatory cells comprises menstrual blood.

8. The method of claim 1, wherein said population of allogeneic cells comprising T regulatory cells comprises adipose derived stromal vascular fraction cells.

\* \* \* \* \*